USO12207934B2

(12) United States Patent
Wright

(10) Patent No.: US 12,207,934 B2
(45) Date of Patent: Jan. 28, 2025

(54) SYSTEM AND METHOD FOR ASSESSMENT AND REHABILITATION OF BALANCE IMPAIRMENT USING VIRTUAL REALITY

(71) Applicant: Temple University-Of The Commonwealth System of Higher Education, Philadelphia, PA (US)

(72) Inventor: William Geoffrey Wright, Philadelphia, PA (US)

(73) Assignee: Temple University-Of The Commonwealth System of Higher Education, Philadelphia, PA (US)

( * ) Notice: Subject to any disclaimer, the term of this patent is extended or adjusted under 35 U.S.C. 154(b) by 964 days.

(21) Appl. No.: 16/479,910

(22) PCT Filed: Jan. 16, 2018

(86) PCT No.: PCT/US2018/013777
§ 371 (c)(1),
(2) Date: Jul. 22, 2019

(87) PCT Pub. No.: WO2018/136386
PCT Pub. Date: Jul. 26, 2018

(65) Prior Publication Data
US 2019/0380638 A1 Dec. 19, 2019

Related U.S. Application Data

(60) Provisional application No. 62/448,451, filed on Jan. 20, 2017.

(51) Int. Cl.
A61B 5/00 (2006.01)
A61B 5/11 (2006.01)
(Continued)

(52) U.S. Cl.
CPC .......... *A61B 5/4023* (2013.01); *A61B 5/0077* (2013.01); *A61B 5/1121* (2013.01);
(Continued)

(58) Field of Classification Search
CPC ... A61B 5/4023; A61B 5/0077; A61B 5/1121; A61B 5/4561; A61B 5/6803; A61B 2562/0219; G06F 3/011; G06T 19/003
See application file for complete search history.

(56) References Cited

U.S. PATENT DOCUMENTS 7,127,376 B2  10/2006  Nashner
7,179,234 B2   2/2007  Nashner
(Continued)

OTHER PUBLICATIONS

B. A. Alsalaheen, A. Mucha, L. O. Morris, S. L. Whitney, J. M. Furman, C. E. Camiolo-Reddy et al., "Vestibular rehabilitation for dizziness and balance disorders after concussion", J Neurol Phys Ther, vol. 34, No. 2, pp. 87-93, Jun. 2010.
(Continued)

*Primary Examiner* — David J. McCrosky
(74) *Attorney, Agent, or Firm* — Riverside Law LLP

(57) ABSTRACT

A method of assessing the balance impairment of a subject includes the steps of presenting the subject with a static scene on a display, collecting a first set of orientation measurements, presenting the subject with an unstable scene on a display, collecting a second set of orientation measurements, storing the first and second sets of orientation measurements on a computing device, referenced to a set of time indices, and calculating a balance score for the subject by comparing the second set of orientation measurements with the first set of orientation measurements. A system for assessing the balance impairment of a subject is also disclosed.

16 Claims, 5 Drawing Sheets

(51) Int. Cl.
  *G06F 3/01* (2006.01)
  *G06T 19/00* (2011.01)
(52) U.S. Cl.
  CPC .......... *A61B 5/4561* (2013.01); *A61B 5/6803* (2013.01); *G06F 3/011* (2013.01); *G06T 19/003* (2013.01); *A61B 2562/0219* (2013.01)

(56) References Cited

U.S. PATENT DOCUMENTS

| | | | |
|---|---|---|---|
| 7,195,355 | B2 | 3/2007 | Nashner |
| 7,500,752 | B2 | 3/2009 | Nashner |
| 8,704,855 | B1 | 4/2014 | Berme |
| 8,847,989 | B1 | 9/2014 | Berme |
| 8,902,249 | B1 | 12/2014 | Wilson |
| 9,081,436 | B1 | 7/2015 | Berme |
| 9,770,203 | B1 | 9/2017 | Berme |
| 9,814,430 | B1 | 11/2017 | Berme |
| 10,413,230 | B1 | 9/2019 | Berme |
| 2006/0264786 | A1 | 11/2006 | Nashner |
| 2007/0047768 | A1 | 3/2007 | Gordon |
| 2011/0152038 | A1* | 6/2011 | Freitag ............... A63B 22/0228 482/54 |
| 2012/0108909 | A1 | 5/2012 | Slobounov |
| 2014/0276130 | A1* | 9/2014 | Mirelman ............... A61B 5/162 600/483 |
| 2014/0302973 | A1 | 10/2014 | Fitterer |
| 2015/0364059 | A1* | 12/2015 | Marks .................... A61B 5/486 482/9 |
| 2017/0000387 | A1* | 1/2017 | Forth ....................... G06N 7/01 |
| 2017/0243346 | A1* | 8/2017 | Hall ........................ A61B 5/458 |
| 2017/0244884 | A1* | 8/2017 | Burtey ................. G02B 27/017 |

OTHER PUBLICATIONS

B. L. Riemann, K. M. Guskiewicz and E. W. Shields, "Relationship between clinical and forceplate measures of postural stability", J Sport Rehabil, vol. 8, pp. 71-82, 1999.

C. S. Baker and M. E. Cinelli, "Visuomotor deficits during locomotion in previously concussed athletes 30 or more days following return to play", Physiol Rep, vol. 2, No. 12, pp. 1-7, Dec. 2014.

D. R. Howell, L. R. Osternig and L. S. Chou, "Return to Activity after Concussion Affects Dual-Task Gait Balance Control Recovery", Med Sci Sports Exerc., Aug. 2014.

D. R. Kaufman, M. J. Puckett, M. J. Smith, K. S. Wilson, R. Cheema and M. R. Landers, "Test-retest reliability and responsiveness of gaze stability and dynamic visual acuity in high school and college football players", Phys Ther Sport, Nov. 2013.

E. A. Keshner, J. Streepey, Y. Dhaher and T. Hain, "Pairing virtual reality with dynamic posturography serves to differentiate between patients experiencing visual vertigo", J Neuroeng Rehabil, vol. 4, pp. 24, 2007.

E. F. Teel and S. M. Slobounov, "Validation of a Virtual Reality Balance Module for Use in Clinical Concussion Assessment and Management", Clin J Sport Med., Jun. 2014.

F. J. Haran, R. Tierney, W. G. Wright, E. Keshner and M. Silter, "Acute changes in postural control after soccer heading", Int J Sports Med., vol. 34, No. 4, pp. 350-354, Apr. 2013.

J. Dichgans, R. Held, L. R. Young and T. Brandt, "Moving visual scenes influence the apparent direction of gravity", Science, vol. 178, pp. 1217-1219, 1972.

J. E. Capo-Aponte, T. G. Urosevich, L. A. Temme, A. K. Tarbett and N. K. Sanghera, "Visual dysfunctions and symptoms during the subacute stage of blast-induced mild traumatic brain injury", Mil Med., vol. 177, No. 7, pp. 804-813, Jul. 2012.

J. K. Register-Mihalik, J. P. Mihalik and K. M. Guskiewicz, "Balance deficits after sports-related concussion in individuals reporting posttraumatic headache", Neurosurgery, vol. 63, pp. 76-80, 2008.

J. M. Gurley, B. D. Hujsak and J. L. Kelly, "Vestibular rehabilitation following mild traumatic brain injury", NeuroRehabilitation, vol. 32, No. 3, pp. 519-528, 2013.

J. R. Lishman and D. N. Lee, "The autonomy of visual kinaesthesis", Perception, vol. 2, No. 3, pp. 287-294, 1973.

J. T. Cavanaugh, K. M. Guskiewicz, C. Giuliani, S. Marshall, V. Mercer and N. Stergiou, "Detecting altered postural control after cerebral concussion in athletes with normal postural stability", Br J Sports Med., vol. 39, pp. 805-811, 2005.

K. D. Brahm, H. M. Wilgenburg, J. Kirby, S. Ingalla, C. Y. Chang and G. L. Goodrich, "Visual Impairment and Dysfunction in Combat-Injured Service members with Traumatic Brain Injury", Optometry Vision Sci., vol. 86, No. 7, pp. 1-9, 2009.

K. G. Harmon, J. A. Drezner, M. Gammons, K. Guskiewicz, M. Halstead, J. S. Kutcher et al., "American Medical Society for Sports Medicine position statement: concussion in sport", Br J Sport Med, vol. 47, pp. 15-26, 2013.

K. Gottshall, A. Drake, N. Gray, E. McDonald and M. E. Hoffer, "Objective vestibular tests as outcome measures in head injury patients", Laryngoscope, vol. 113, No. 10, pp. 1746-1750, 2003.

K. M. Guskiewicz, B. L. Riemann, D. H. Perrin and L. M. Nashner, "Alternative approaches to the assessment of mild head injury in athletes", Med Sci Sports Exerc., vol. 29, No. 7 Suppl, pp. S213-21, Jul. 1997.

K. M. Guskiewicz, S. E. Ross and S. W. Marshall, "Postural stability and neuropsychological deficits after concussion in collegiate athletes", J Athl Train., vol. 36, pp. 263-273, 2001.

K. R. Gottshall and M. E. Hoffer, "Tracking recovery of vestibular function in individuals with blast-induced head trauma using vestibular-visual-cognitive interaction tests", J Neurol Phys Ther, vol. 34, No. 2, pp. 94-97, Jun. 2010.

M. H. Heitger, R. D. Jones, A. D. Macleod, D. L. Snell, C. M. Frampton and T. J. Anderson, "Impaired eye movements in post-concussion syndrome indicate suboptimal brain function beyond the influence of depression malingering or intellectual ability", Brain, vol. 132, pp. 2850-2870, Oct. 2009.

M. H. Heitger, R. D. Jones, J. C. Dalrymple-Alford, C. M. Frampton, M. W. Ardagh and T. J. Anderson, "Motor deficits and recovery during the first year following mild closed head injury", Brain Inj, vol. 20, pp. 807-824, 2006.

M. McCrea, K. M. Guskiewicz, S. W. Marshall, W. Barr, C. Randolph et al., "Acute effects and recovery time following concussion in collegiate football players: the NCAA concussion study", JAMA, vol. 290, pp. 2556-2563, 2003.

M. R. Scherer, H. Burrows, R. Pinto, p. Littlefield, L. M. French, A. K. Tarbett et al., "Evidence of central and peripheral vestibular pathology in blast-related traumatic brain injury", Otol Neurotol., vol. 32, No. 4, pp. 571-580, Jun. 2011.

N. Kapoor and K. J. Ciuffreda, "Vision Disturbances Following Traumatic Brain Injury", Curr Treat Options Neurol, vol. 4, No. 4, pp. 271-280, 2002.

N. Murray, A. Salvatore, D. Powell and R. Reed-Jones, "Reliability and validity evidence of multiple balance assessments in athletes with a concusison", J Athl Train., vol. 49, No. 4, pp. 540-549, 2014.

P. McCrory, W. Meeuwisse, M. Aubry, R. Cantu, J. Dvorak and R. J. Echmendia, Consensus statement on concussion in sport: the 4th international conference on concussion in sport held in Zurich Nov. 2012. Br J Sport Med, vol. 47, pp. 250-258, 2013.

R. A. Clark, A. L. Bryant, Y. Pua, p. McCrory, K. Bennell and M. Hunt, "Validity and reliability of the Nintendo Wii Balance Board for assessment of standing balance", Gait Posture, vol. 31, No. 3, pp. 307-310, 2010.

S. M. Jacobs and G. P. Van Stavem, "Neuro-ophthalmic deficits after head trauma", Curr Neurol Neurosci Rep, vol. 13, No. 11, p. 389, Nov. 2013.

W. G. Wright, J. McDevitt and K. O. Appiah-Kubi, "A portable virtual reality balance device to assess mild traumatic brain injury symptoms: A pilot validation study," 2015 International Conference on Virtual Rehabilitation (ICVR), 2015, pp. 72-79, doi: 10.1109/ICVR.2015.7358591.

W. Young, S. Ferguson, S. Brault and C. Craig, "Assessing and training standing balance in older adults: A novel approach using the 'Nintendo Wii' Balance Board", Gait Posture, 2010.

(56) References Cited

OTHER PUBLICATIONS

Akbari, Asghar, et al. "The effects of balance training on static and dynamic postural stability indices after acute ACL reconstruction." Global journal of health science 8.4 (2016): 68.

Halabchi, Farzin, et al. "Comparison of static and dynamic balance in male football and basketball players." Foot & ankle specialist 13.3 (2020): 228-235.

Rizzato, Alex, et al. "Are static and dynamic postural balance assessments two sides of the same coin? A cross-sectional study in the older adults." Frontiers in Physiology 12 (2021): 681370.

Rubega, Maria, et al. "Cortical correlates in upright dynamic and static balance in the elderly." Scientific Reports 11.1 (2021): 1-15.

\* cited by examiner

SYSTEM AND METHOD FOR ASSESSMENT AND REHABILITATION OF BALANCE IMPAIRMENT USING VIRTUAL REALITY

CROSS-REFERENCE TO RELATED APPLICATIONS

This application is a national stage filing of International Patent Application No. PCT/US18/13777, filed Jan. 16, 2018, which claims priority to U.S. Provisional Patent Application No. 62/448,451 filed on Jan. 20, 2017, both of which are incorporated herein by reference in their entireties.

STATEMENT REGARDING FEDERALLY SPONSORED RESEARCH OR DEVELOPMENT

This invention was made with government support under W81XWH-13-C-0189 awarded by the Medical Research and Development Command. The government has certain rights in the invention.

BACKGROUND OF THE INVENTION

Balance impairment is a condition that causes people to feel unsteady or dizzy. For example, if a subject is standing or walking, they may feel like they are unsteady or tipping over. If a subject is sitting or lying down, they may feel like they are moving, spinning or floating. These sensations could also be accompanied by feelings of anxiousness or wooziness. A proper sense of balance results from the coordination of several body systems, including the visual system (eyes), vestibular system (inner ears) and somatosensory system (the body's sense of itself and where it is in space). Degeneration or loss of function in any of these systems can lead to balance deficits.

One popular cause of balance impairment is a concussion or other traumatic brain injury (TBI). Standard methods of care for a concussion involve rest and gradual reintroduction to the activities of daily living. The duration of rest and speed of reintroduction are difficult to meter, because of the subjective nature of many symptoms of brain injury. Postural stability is a highly sensitive biomarker for brain injury or disease, and healthcare professionals currently use limited testing in controlled settings for clinical measurement of balance impairment. However, when subjected to repeat testing, patients often learn to compensate for repeated, single-task clinical measurement techniques.

The industry standard for assessing balance impairment across all domains of neurological pathologies typically involves expensive capital equipment. For example, one well known system called the Neurocom Smartbalance Master (Natus Medical) can cost $70K-150K, depending on the model. One existing system uses a lower-cost approach while improving system reliability and sensitivity. See for example Wright et al., "A portable virtual reality balance device to assess mild traumatic brain injury symptoms: A pilot validation study." IEEE Proc ICVR 2015, pp 72-79, and Wright et al., "Assessing subacute mild traumatic brain injury with a portable virtual reality balance device." Disability and Rehabilitation, 10:1-9, which are incorporated herein by reference in their entirety. This virtual reality based balance assessment system requires a force plate (e.g. Wii balance board), a large-screen television and a software user interface to collect and process data. However, these conventional systems have a few drawbacks. The systems require a large footprint, since the set-up has to be large enough to accommodate the subject and evaluation equipment. To this end, the conventional system has several different large and bulky components that require some effort to move and set up. Further, the subject's perception of the images on the large screen are limited by the fact that the subject knows they are looking at a screen and can utilize peripheral visual information to override the visual scene displayed on the television screen. The subject's reaction to images on the screen are therefore not as authentic as if, for example, the subject felt like they were reacting to something in the "real" environment.

Thus, what is needed in the art is an improved system for evaluating balance impairment that is highly portable, self-contained, low cost, more realistic to the subject, and provides improved system reliability and sensitivity. Further, the system should be easily adaptable for and compatible with applications for clinical purposes, such as oculomotor and vestibulo-ocular training, PTSD exposure treatment, phobic desensitization and pain management.

SUMMARY OF THE INVENTION

In one aspect, a device for assessing the balance impairment of a subject comprises a head-mounted display (HMD) comprising a set of at least one display panels, an orientation sensor, a computing device, and a non-transitory computer readable medium with instructions stored thereon, that when executed by a processor, perform a method comprising the steps of presenting a sequence of scene protocols to the set of at least one display panels, recording a set of measurements from the orientation sensor and a set of time indices during the sequence of scene protocols, and calculating a balance score by referencing the set of measurements from the orientation sensors and the set of time indices to the sequence of scene protocols.

In one embodiment, the device further comprises a pad, wherein the pad comprises a soft material and wherein the pad is designed to impede the subject from maintaining balance. In one embodiment, the device further comprises a camera, wherein the computing device further records a set of camera frames from the camera; and wherein the computing device further refines the calculated balance score by evaluating the set of camera frames referenced to the sequence of scene protocols. In one embodiment, the camera is physically attached to the display or an earth-fixed location.

In another aspect, a method of assessing the balance impairment of a subject comprises the steps of presenting the subject with a static scene on a display, collecting a first set of orientation measurements, presenting the subject with an unstable scene on the display, collecting a second set of orientation measurements, storing the first and second sets of orientation measurements on a computing device, referenced to a set of time indices, and calculating a balance score for the subject by comparing the second set of orientation measurements with the first set of orientation measurements.

In one embodiment, the display is a head-mounted display. In one embodiment, the display is an LCD display having a display size greater than 21 inches, positioned in front of the subject. In one embodiment, the display is a plurality of LCD displays positioned around the subject. In one embodiment, the display comprises at least one projector configured to project an image on a surface positioned in front of the subject. In one embodiment, the at least one projector is configured for rear projection, and the surface is positioned between the projector and the subject. In one embodiment, the static scene is a blank screen. In one embodiment, the static scene is a virtual reality scene. In one embodiment, the set of orientation measurements is captured at a rate of approximately 100 Hz.

In one embodiment, the method further comprises the steps of positioning the subject on an unstable surface, presenting the subject with an unstable scene on a display, collecting a third set of orientation measurements, and calculating a refined balance score for the subject by comparing the third set of orientation measurements to the second set of orientation measurements. In one embodiment, the method further comprising the steps of capturing a set of images from a camera, performing a set of image processing operations on the set of images, and computing a refined balance score based on an output of the set of image processing operations.

In another aspect, a method for improving postural function in a subject comprises the steps of fitting an augmented reality headset on a subject, superimposing a fixed reference point on a scene presented to the subject on the augmented reality headset, monitoring a set of orientation parameters gathered from a set of at least one sensor fixedly attached to a subject, calculating a postural deficiency from the set of orientation parameters, creating an unstable scene by adjusting the position of the fixed reference point based on the set of orientation parameters, and altering the dependency of the subject's postural control system on the visual display, correcting the postural deficiency.

In one embodiment, the method further comprises the steps of positioning the subject on an unstable surface, and altering the dependency of the subject's postural system on the subject's somatosensory input, correcting the postural deficiency. In one embodiment, the method further comprises the steps of monitoring a second set of orientation parameters gathered from a second set of at least one sensor positioned remotely from the subject, and supplementing the calculation of the postural deficiency with the second set of orientation parameters. In one embodiment, the second set of at least one sensor comprises a camera. In one embodiment, at least one sensor is selected from a group consisting of an accelerometer, a gyroscope, and a magnetometer.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION OF THE INVENTION

Figure 1:
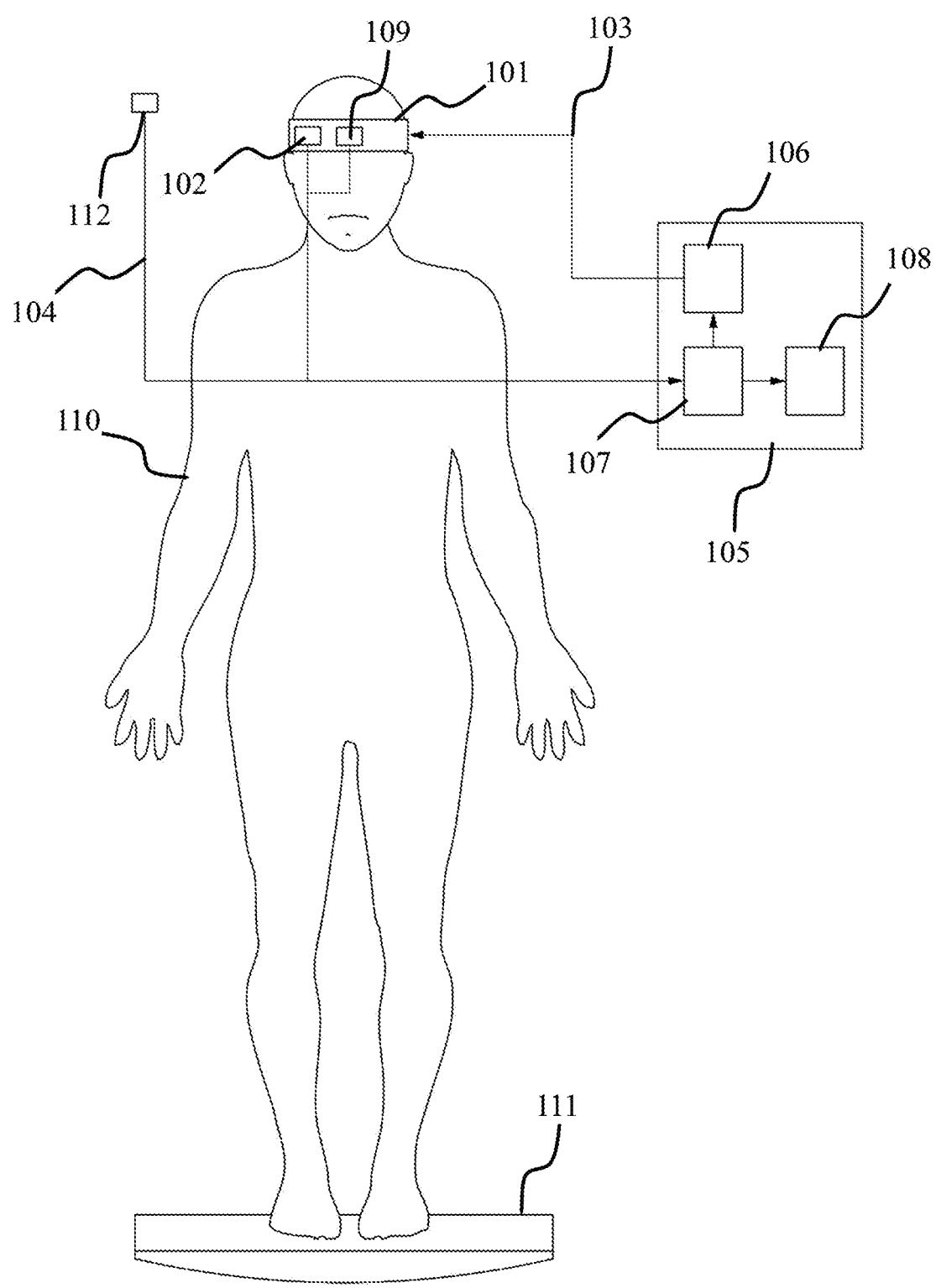
FIG. 1 is a schematic of an exemplary system of the present invention according to one embodiment.

It is to be understood that the figures and descriptions of the present invention have been simplified to illustrate elements that are relevant for a more clear comprehension of the present invention, while eliminating, for the purpose of clarity, many other elements found in systems and methods of assessment and rehabilitation of brain injuries using virtual reality. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of +20%, +10%, +5%, +1%, and +0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

In some aspects of the present invention, software executing the instructions provided herein may be stored on a non-transitory computer-readable medium, wherein the software performs some or all of the steps of the present invention when executed on a processor.

Aspects of the invention relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled or interpreted, including but not limited to C, C++, C#, Objective-C, Java, JavaScript, Python, PHP, Perl, Ruby, or Visual Basic. It is further understood that elements of the present invention may be executed on any acceptable computing platform, including but not limited to a server, a cloud instance, a workstation, a thin client, a mobile device, an embedded microcontroller, a television, or any other suitable computing device known in the art.

Parts of this invention are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G or 4G/LTE networks, Bluetooth®, Bluetooth® Low Energy (BLE) or Zigbee® communication links, or any other method by which one electronic device is capable of communicating with another. In some embodiments, elements of the networked portion of the invention may be implemented over a Virtual Private Network (VPN).

As used herein, the abbreviation "HMD" may be used to indicate a head-mounted display, which includes any display or set of displays positioned such that the display area covers the field of view of one or both of the eyes of a subject and that the device is fixed to the head. Examples of HMDs include the Oculus Rift or HTC Vive, as well as self-contained smartphone driven HMDs such as Samsung Galaxy Gear, LG 360 VR, or Google Cardboard devices, all of which use estimates of head position and orientation to update the virtual scene in earth-fixed coordinates.

As used herein and unless specified otherwise, certain abbreviations known in the art of computing will be defined as follows: "GUI" will be used to indicate a graphical user interface. "USB" may refer to the Universal Serial Bus protocol or, alternatively, to a physical cable used to communicate data via the Universal Serial Bus protocol. "HDMI" refers to the High-Definition Multimedia Interface or, alternatively, to any physical cable used to communicate data via the High-Definition Multimedia interface. The abbreviations LAN and WAN denote Local-Area Network and Wide-Area Network, respectively.

Head movement is described, using the terms "roll", "pitch", and "yaw". As defined herein, "roll" is understood to mean rotation of the head about the line parallel to the subject's naso-occipital axis, "pitch" is understood to mean rotation of the head about the axis running ear-to-ear, and "yaw" is understood to mean rotation of the head about the axis orthogonal to the other two axes (i.e. the cross-product of the "roll" and "pitch" axes forms the "yaw" axis). While these terms are described in egocentric coordinates, the update of the virtual scene in most HMDs is with respect to earth-fixed coordinates. Depending on the orientation of the wearer the yaw axis may be in parallel with earth-fixed vertical.

Referring now in detail to the drawings, in which like reference numerals indicate like parts or elements throughout the several views, in various embodiments, presented herein is a system and method for assessment and rehabilitation of balance impairment using virtual reality.

With reference now to FIG. 1, the present invention comprises an HMD 101 to be worn by a subject 110. The HMD 101 may preferably comprise two separate displays, arranged such that each occupies most or all of the field of view of one of the subject's eyes. The HMD may optionally comprise only a single display, with the perspective for one eye displayed on one half of the display and the perspective for the other eye displayed on the other half of the display. In some embodiments, the image displayed to the subject's right eye is different from the image displayed to the subject's left eye, in order to produce a stereoscopic illusion of depth. In other embodiments, the image displayed to the subject's left eye is the same as the image displayed to the subject's right eye. The imagery shown on the one or more displays in the HMD 101 is rendered on a computing device 105, specifically using a graphics engine 106. The graphics engine 106 can be any graphics engine known in the art. In some embodiments, the graphics engine 106 is the Unity graphics engine. In some embodiments, the graphics engine is a smartphone. In some embodiments, a smartphone serves multiple roles within the system, including but not limited to the role of the graphics engine 106, the LED 109, the computing device 105, or the orientation sensor 102. The image data is conveyed to the one or more displays in the HMD via a data link 103. In some embodiments, the data link 103 comprises a physical connection, such as an HDMI, composite, or VGA cable. In other embodiments, the data link 103 comprises a wireless connection, such as video data streamed over 802.11 wi-fi, or a specialized wireless display protocol such as wireless HDMI. The display resolution of the image data is preferably high, and may be 1080p, 2160p, or any other suitable display resolution known in the art. In an exemplary embodiment, the pixel density of the HMD is sufficiently high that a person with average visual acuity cannot see the boundaries between adjacent pixels while wearing the HMD.

In some embodiments, the HMD 101 comprises an orientation sensor 102 and one or more LEDs 109, connected to a computing device 105 via a data link 104. In the exemplary embodiment, the orientation sensor 102 and the one or more LEDs 109 are physically and rigidly connected to the HMD 101, in order to guarantee that orientation data derived from them is valid with respect to the HMD. In an exemplary embodiment, the data link 103 for the one or more displays is shared with the data link 104 for the sensors. In other embodiments, the data link 104 for the sensors is a separate dedicated link. In one embodiment, the data link 104 for the sensors is a USB connection. In other embodiments, the data link 104 for the sensors is a wireless protocol, for example Bluetooth or 802.11 wi-fi. In some embodiments, the orientation sensor 102 is an accelerometer. In some embodiments, the orientation sensor 102 comprises a gyroscopic sensor. In some embodiments, the orientation sensor 102 provides physical orientation data of the HMD as a set of Euler angles. In some embodiments, the orientation sensor 102 provides orientation data of the HMD as a set of quaternions. It is understood by those skilled in the art that a typical accelerometer-based orientation sensor calculates orientation by calculating the acceleration vector of Earth's gravity, but the present invention may also use any other orientation-measurement system known in the art. For example, the Oculus Rift HMD system uses predictive tracking algorithms and a high-sampling rate microelectromechanical (MEMS) inertial measurement unit to sense and filter head orientation and motion, which is used to update and render the virtual visual scene. The MEMS unit includes three-axis gyroscopes, accelerometers, and magnetometers and the predictive tracking reduces the time lag in updating the visual scene. This includes head tilt correction with complementary filtering which takes advantage of the low drift in the gyro at high frequency and the low drift of the accelerometers at low frequency. In some embodiments, the one or more cameras 112 record the position over time of the one or more LEDs 109 to provide positional data to the head. In an exemplary embodiment, the camera data is subjected to optical flow image processing in order to provide additional data about the orientation of the HMD over time.

Typical HMD applications modify a displayed viewing angle of a static or dynamic three-dimensional environment in order to compensate for changes to head orientation, thus creating the illusion that the user is "looking around" the environment. However, for the purposes of the present invention, it is understood that the displayed image or images may also be programmed to move independently from the sensor data, for example in a way that does not directly compensate for changes to head orientation.

Although embodiments of the invention are described herein as including a head-mounted display, it is understood that some embodiments could additionally or alternatively include one or more displays mounted to other parts of a subject's body, including but not limited to the neck, arm, chest, leg, abdomen, hand, or any other suitable part of the subject's body.

The invention further comprises a sensor data processing engine 107 and a logging engine 108. The sensor data processing engine 107 accepts data from the orientation sensor 102 and the one or more cameras 112. In some embodiments, the sensor data processing engine 107 is a software program running on the computing device 105. In other embodiments, the sensor data is processed wholly or partially on a second computing device. The second computing device may be another computer system, or may be a dedicated single-board computer, or other microcontroller or processor. In some embodiments, the sensor data is processed wholly or partially on a field programmable gate array (FPGA). Preferably, the sensor data is sampled at approximately 100 Hz, but in some embodiments the sampling rate may be as low as 20 Hz. In other embodiments, the sensor data is sampled at other frequencies higher than 100 Hz. As understood by those skilled in the art, the sampling rate should be at least twice the rate of the highest frequency component desired to be measured, or the Nyquist frequency. In some embodiments, the sensor data processing engine translates Euler angles into quaternions, or vice-versa. In some embodiments, the sensor data processing engine computes optical flow or performs object recognition or other image-processing algorithms on the visual data received from the one or more cameras 112. In some embodiments, the processed output of the sensor data processing engine is conveyed to the graphics engine 106 to modify the perspective displayed on the HMD. For example, received sensor data indicating that the HMD has turned in a clockwise yaw may rotate the perspective of the scene displayed to the subject in a corresponding compensatory counter-clockwise yaw. In this way, any movements of the subject 110's head will be reflected in the displayed scene, and the subject will believe that he or she is looking around a virtual scene that is entrained to the subject's movements rather than simply watching images displayed on one or more screens.

The logging engine 108 may accept data from the orientation sensor 102, the one or more cameras 112, and any other sensing peripherals or software capable of producing data in the system. The logging engine may accept, for example, timestamped execution log information from the graphics engine, so that the timestamps of the sequence of scene protocols and the timestamps of the orientation sensor data may be recorded at the same point in the execution path. The logging engine may then record some or all of the data accepted into a log output, which may comprise a set of text files or binary files stored on a non-volatile storage medium. In other embodiments, the accepted data may be recorded as entries in a database, on the same or on a second remote computing device.

The graphics engine 106 also accepts as input a sequence of scene protocols for performing the evaluation. An exemplary list of scene protocols comprises a dark scene, a stable scene, and an unstable scene. As contemplated herein, a "stable scene" may refer either to a static image (i.e. the image displayed on the HMD does not change over time) or a static scene (i.e. the image displayed on the HMD changes only in response to movement of the subject's head, in order to simulate the sensation of looking around a virtual environment). As contemplated herein, an "unstable scene" may refer either to an image or view of a scene that changes arbitrarily and ignores any orientation input from the HMD or an image or view of a scene that changes both arbitrarily and in response to orientation input from the HMD. During evaluation, the subject attempts to maintain postural stability during the various scene protocols. Postural stability may be measured by one or more orientation sensors and cameras attached to the HMD, or may alternatively be measured by a pressure sensing pad or board on which the subject stands during evaluation.

In some embodiments, the invention further comprises a pad comprising foam or some other material 111, positioned such that the subject 110 stands on the pad 111 during some or all parts of the evaluation. Although the pad is a foam pad in the depicted embodiment, the pad may comprise any material or materials such that the subject 110 has difficulty maintaining a stable footing while standing on the pad. An exemplary foam pad is the Airex Balance-pad (Sins, Switzerland), which has the characteristics of a unique polyurethane close-cell material with 30-60 kg/m$^3$ density and thickness between 5-10 cm and has been shown to significantly affect postural control. The pad is described in Lin C C, Roche J L, Steed D P, Musolino M C, Marchetti G F, Furman G R, Redfern M S, Whitney S L. Test-retest reliability of postural stability on two different foam pads. *J Nat Sci.* 2015 Feb. 1;1 (2): e43, which is incorporated herein by reference in its entirety.

In some embodiments, the invention further comprises one or more additional cameras 112 positioned separately from the HMD, and pointed at the subject 110. These one or more additional cameras record the posture and position of the subject during testing, and provide supplemental data about posture stability to refine the results from the orientation sensor 102 and the one or more cameras 112. The one or more additional cameras 112 may be connected to the computing device 105 by the data link 104, or by a second, similar data link to the data link 104.

Figure 2:
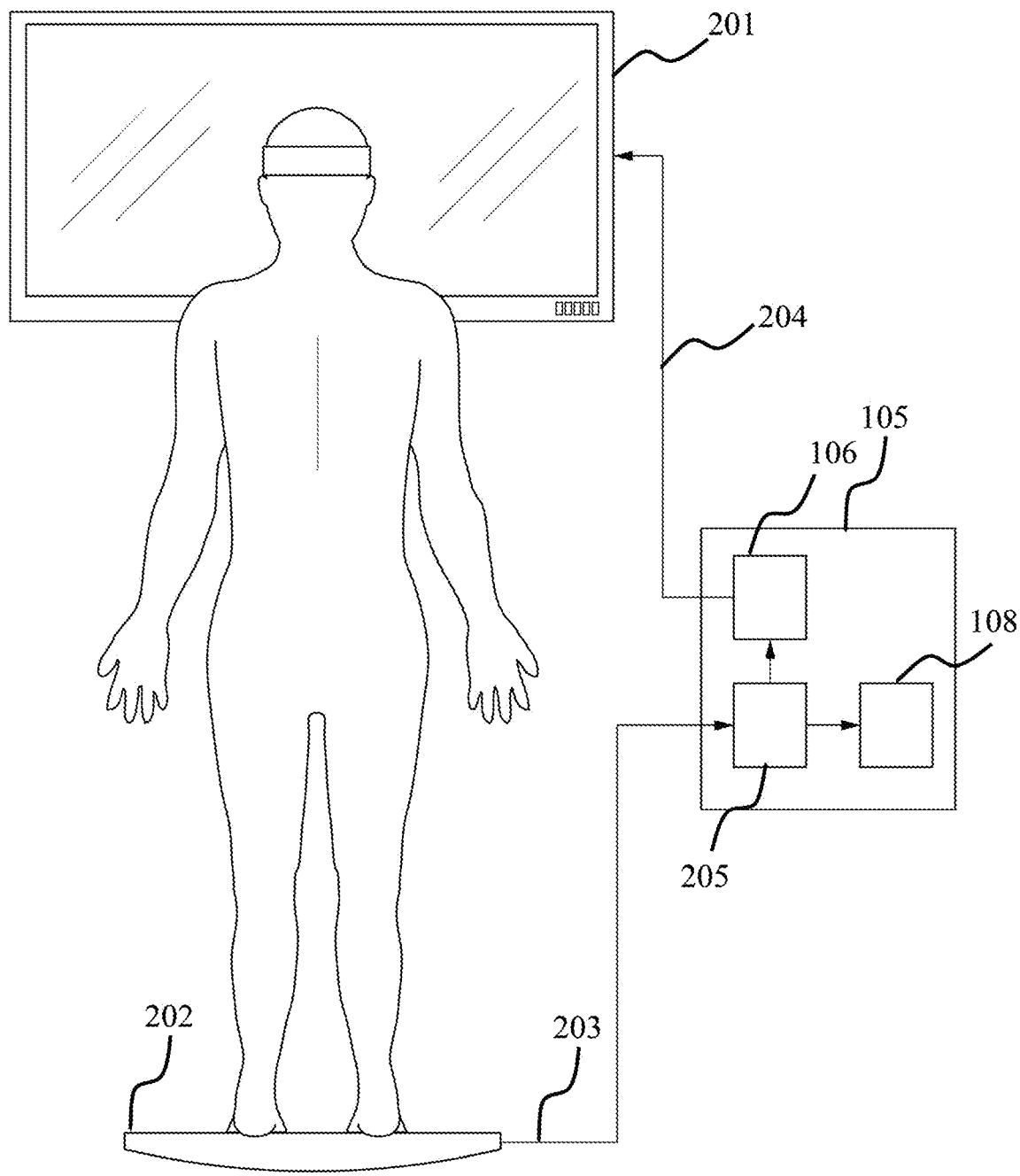
FIG. 2 is another embodiment of the system of the present invention according to one embodiment.

Referring now to FIG. 2, an alternative embodiment of the invention comprises a standalone screen 201 in place of the HMD. Instead of wearing the HMD during evaluation, the subject positions herself in front of the screen 201 such that the screen occupies the majority of the subject's field of view. This embodiment of the invention may be beneficial for subjects who have difficulty with HMDs. In some embodiments, multiple screens may be used, positioned at different angles around the subject in order to occupy more of the subject's field of view. In some embodiments, one or more of the mounted screens are themselves curved instead of being flat.

One or more projectors may also be used in addition to or in place of the flat panel displays. Projectors may project on one or more flat surfaces, one or more curved surfaces, or on a single, spherically curved surface. In some embodiments, multiple projectors are used and their projection areas are overlaid with one another to eliminate seams. The display brightness of some or all overlaid projectors may be modulated across the area of the projection in order to compensate for brighter patches where two projection areas intersect. In some embodiments, one or more projectors may be fixedly attached to the subject's head, with the projected image changing in order to follow the subject's head orientation, similarly to the way head mounted displays do. Suitable projectors include, but are not limited to, LED projectors, DLP projectors, LCD projectors, pico projectors, or any other suitable projector known in the art. Projectors may be arranged with lensing and screens to project on the rear of the screen or the front of the screen, and may be short-throw projectors, medium-throw projectors, or long-throw projectors.

In some embodiments, a subject's balance shifting may be measured by one or more orientation sensors and one or more cameras similar to 102 and 112 in FIG. 1, but here separately connected to the subject's head, legs, or other parts of the body as may be beneficial for measuring posture stability. In other alternative embodiments, the system may also use a pressure sensing platform 202 to measure a subject's weight distribution, connected by a data link 203 to the computing device 105. One example of a pressure sensing platform 202 is a Wii Balance Board. In some embodiments, the pressure sensing platform 202 also comprises the pad comprising foam or some other material 111 as shown in FIG. 1. In the exemplary embodiment shown in FIG. 1, the measurement and presentation portions of the invention are consolidated into the HMD, eliminating the need for the pressure sensing platform 202 and the stand-alone screen 201.

An augmented-reality (AR) system may also be used, in conjunction with an AR-capable HMD, for example, but not limited to, Google Glass or Microsoft HoloLens. For example, a subject may wear an AR HMD, which then superimposes a visual indicator for a fixed reference point somewhere in the room the subject is standing in. In some embodiments, the fixed reference point is used to aid the user's balance. In some embodiments, the fixed reference point is instead a moving reference point. In some embodiments, the AR display scene can be uncoupled with the orientation sensors to create visual-vestibular discordance. In some embodiments, the AR display can be used to superimpose dynamic visual input over the real scene. These embodiments can be used to diagnose postural or sensory impairments in much the same way the moving scenery does in the embodiment of FIG. 1. These embodiments can also be used for altering the postural control system in rehabilitation applications.

Figure 3:
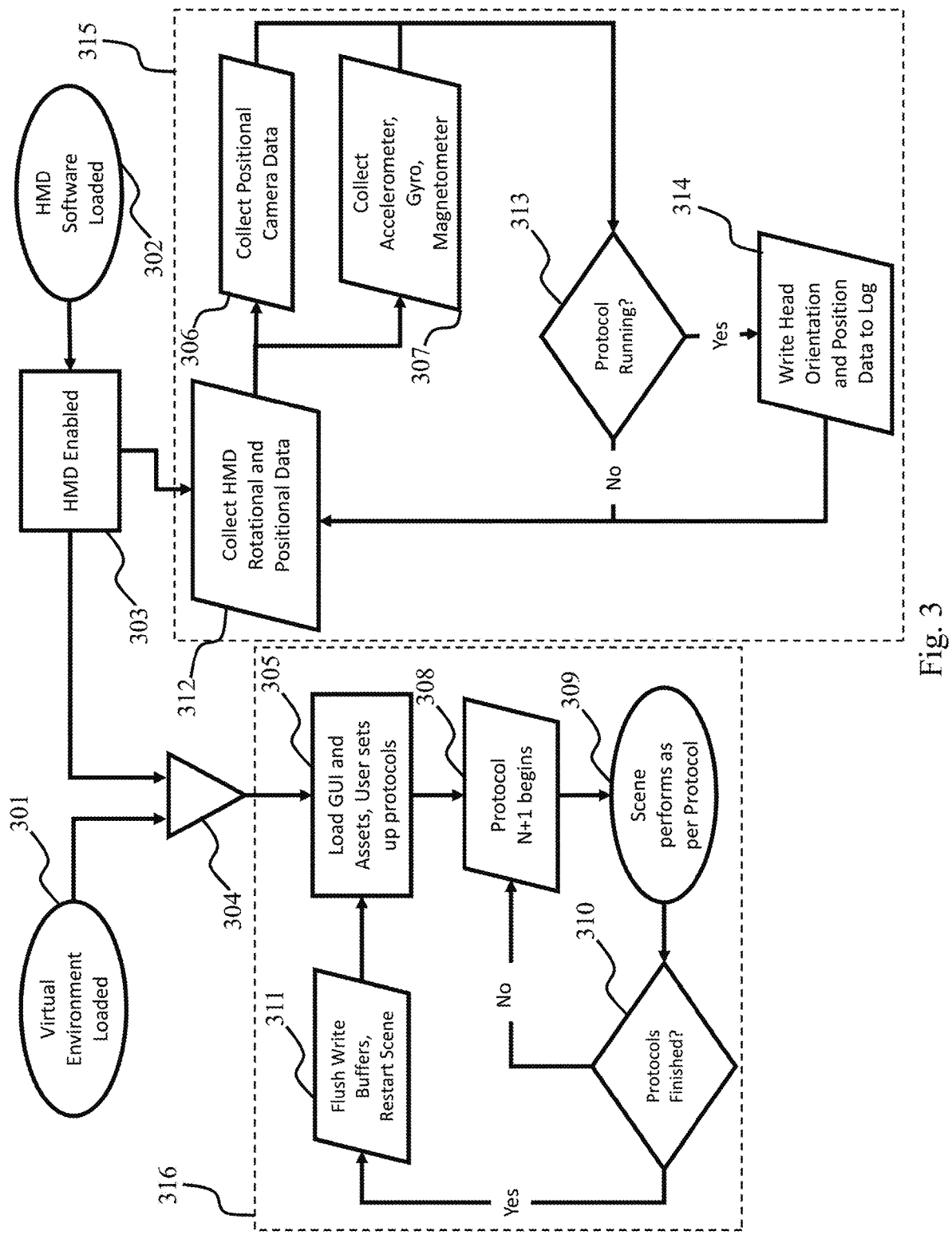
FIG. 3 is a diagram of exemplary software processing steps of the present invention according to one embodiment.

Referring now in detail to FIG. 3, an exemplary embodiment of processing flow for a balance assessment and rehabilitation system is shown. At initialization, the Virtual Environment is loaded 301, and the HMD Software is loaded 302. When both the HMD is enabled 303 and the Virtual Environment is fully loaded 301, the user interface is initialized so that the subject can select which protocol or protocols will be evaluated 305. In parallel, the system begins collecting data 312 from the at least one orientation sensor 102. This begins the data processing loop 315. In addition to the orientation sensor data, the system begins collecting camera data 306 and accelerometer, gyroscope, and magnetometer data 307. In some embodiments, the data is collected serially, but in one embodiment, the camera data 306 and accelerometer, gyro, and magnetometer data are collected in parallel. Once a set of data is collected, the system checks to see if a protocol is running 313. If a protocol is found to be running, the data collection loop writes the collected and processed data to a log 314. In some embodiments, the data collection processing loop also comprises the step of calculating the coordinate transformations from earth-fixed coordinates to subject-fixed coordinates. In some embodiments, the data collection loop also comprises the steps of calculating the variability of the coordinate measurements, and plotting the data as an ellipsoid for further analysis. In various embodiments, the data collected may include some or all of the following data types: Euler angles, quaternions, sway area or volume, sway velocity, sway variability, center of pressure (hereinafter "COP") coordinates, COP velocity, COP sway area, and any other intermediate data types known in the art as are necessary to calculate this list of data types. The log data can be recorded locally to the same computer system that is executing the Virtual environment, or may be transmitted over a LAN or WAN to another computer, using any data transport protocol known in the art. The logged data may be stored as a file in a file system or in a software database. Following the optional logging step, execution returns to the beginning of the data collection loop and a new set of data is collected 312.

Running separately from the data collection loop 315 is the presentation loop 316. The presentation loop comprises the steps of loading the GUI and setting up the scene protocols 305, then stepping through the list of protocols 308, updating the scene as appropriate to each protocol 309, and checking to see if the end of the list of protocols has been reached 310. At the completion of a given protocol, if there are more protocols in the list, the presentation loop moves to the next protocol in the list 308 and repeats the steps 309 and 310 until reaching the end of the list of protocols. Once the end of the list has been reached, the presentation loop flushes the write buffers and restarts the scene 311, presenting to the subject and/or operator the GUI 305 once again.

The computer operable component(s) of the system may reside entirely on a single computing device, or may reside on a central server and run on any number of end-user devices via a communications network. The computing devices may include at least one processor, standard input and output devices, as well as all hardware and software typically found on computing devices for storing data and running programs, and for sending and receiving data over a network, if needed. The computing device(s) may also be connected directly or via a network to allow for the communication of files, email, software, and any other data format between two or more computing devices. The communications network can be a wide area network and may be any suitable networked system understood by those having ordinary skill in the art, such as, for example, an open, wide area network (e.g., the Internet), an electronic network, an optical network, a wireless network, a physically secure network or virtual private network, and any combinations thereof. The communications network may also include any intermediate nodes, such as gateways, routers, bridges, internet service provider networks, public-switched telephone networks, proxy servers, firewalls, and the like, such that the communications network may be suitable for the transmission of information items and other data throughout the system.

The communications network may use standard architecture and protocols as understood by those skilled in the art, such as, for example, a packet switched network for transporting information and packets in accordance with a standard transmission control protocol/Internet protocol ("TCP/IP"). Any of the computing devices may be communicatively connected into the communications network through, for example, a traditional telephone service connection using a conventional modem, an integrated services digital network ("ISDN"), a cable connection including a data over cable system interface specification ("DOCSIS") cable modem, a digital subscriber line ("DSL"), a T1 line, or any other mechanism as understood by those skilled in the art. Additionally, the system may utilize any conventional operating platform or combination of platforms (Windows, Mac OS, Unix, Linux, Android, etc.) and may utilize any conventional networking and communications software as would be understood by those skilled in the art.

Figure 4:
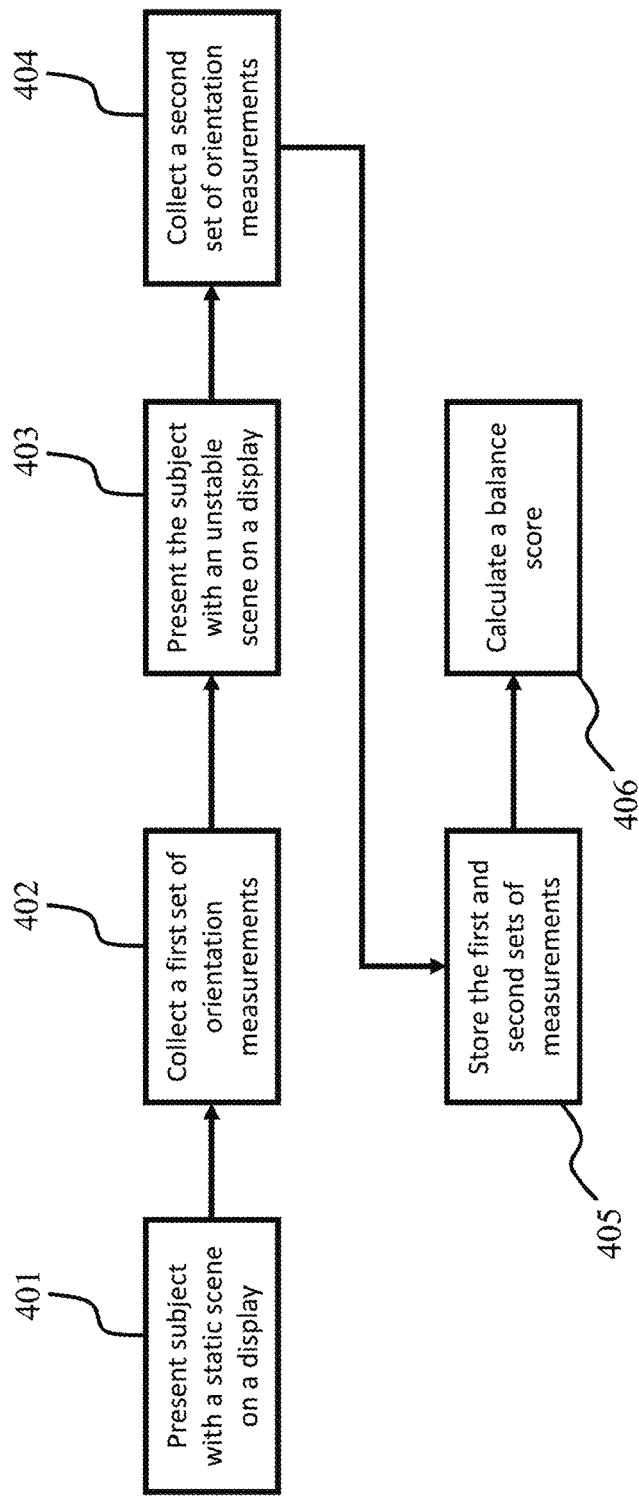
FIG. 4 is a flow diagram of an exemplary method of the present invention according to one embodiment.

This invention also includes a method of assessing the balance impairment of a subject. As shown in FIG. 4, the method comprises the steps of presenting the subject with a static scene on a display 401, collecting a first set of orientation measurements 402, presenting the subject with an unstable scene on a display 403, collecting a second set of orientation measurements 404, storing the first and second sets of orientation measurements on a computing device referenced to a set of time indices 405, and calculating a balance score for the subject by comparing the second set of orientation measurements with the first set of orientation measurements 406.

Dynamic Virtual Reality exposure is a sensitive and specific condition for discriminating individuals with concussions or other traumatic brain injuries from healthy individuals. Those putatively recovered may still have symptoms, which the device and method of the present invention can detect. In an exemplary embodiment, the dynamic VR exposure comprises an unstable VR scene wherein the scene is rotated about the "roll" axis. In some embodiments, the rate of roll is 60 degrees per second. Though the roll axis is preferred in some cases, the invention also includes embodiments wherein the scene is rotated about the "yaw" and "pitch" axes. The invention also includes unstable VR scenes wherein the scene is rotated around a combination of the roll, pitch, and yaw axes.

Although the exemplary use of this invention is evaluation of traumatic brain injury symptoms, the method described herein may also be applied to other therapeutic and diagnostic scenarios, including but not limited to post-concussive syndrome, multisensory processing defects, PTSD exposure treatment, phobic desensitization, pain management, and balance assessment for the elderly, Parkinson's Disease, cerebellar ataxia, and other neuropathologies with balance impairment. Athletes, members of the military, and the elderly may all benefit from treatments and diagnostic services facilitated by the present invention. In addition to diagnosis as provided above, the invention may be used for rehabilitation. A patient suffering from subacute post-concussion symptoms may be gradually reintroduced to dynamic VR scenes, analogous to a "titrated dosage." Such gradual reintroduction ultimately rehabilitates the patient's visual-vestibular processing deficits and returns the patient to pre-injury health status.

Further uses of systems and methods of the present invention include uses in education, for example immersive learning applications. In one embodiment, visual deficits can be simulated for the purposes of training. For example, the visual display can be uncoupled from the orientation sensor input to simulate visual-vestibular deficits for the purposes of training. In one embodiment, the balance assessment protocol can be used for training how the postural system functions in healthy and injured individuals.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Using an inverted single link pendulum model movement of the head, it can be shown that head movements strongly correlate with movement of the center of mass (COM) and center of pressure (COP). Postural control involves maintaining the COM within the base-of-support (BOS). BOS with regards to postural control is defined by the points of contact providing physical support to a person's postural stability, which also meet the requirement of exceeding a mechanical threshold. The BOS in an individual who is standing upright with their two feet together on the ground and no other contact points with surrounding support surfaces would be defined by the area outlined by their two feet. Alternatively, if one were using a cane, the BOS would encompass the area defined by these three points of contact, i.e. two feet and one cane. To maintain postural stability an individual uses feedback from the somatosensory system (e.g. tactile input from foot soles, joint and muscle input from feet, ankles, knees, hips, trunk, neck, etc.), the visual system (e.g. orientation and optic flow input), and the vestibular system (e.g. gravitoinertial orientation, linear and angular motion input), which may individually or together through neural integration generate motor output that is applied to the support surface in order to keep the COM from leaving the BOS which defines one's limits of stability (LOS).

However, even if the body is not treated as an inverted pendulum current evidence suggests that linear and angular translation of the head, as detected by sensors placed on the head, can be used to detect postural stability.

Figure 5:
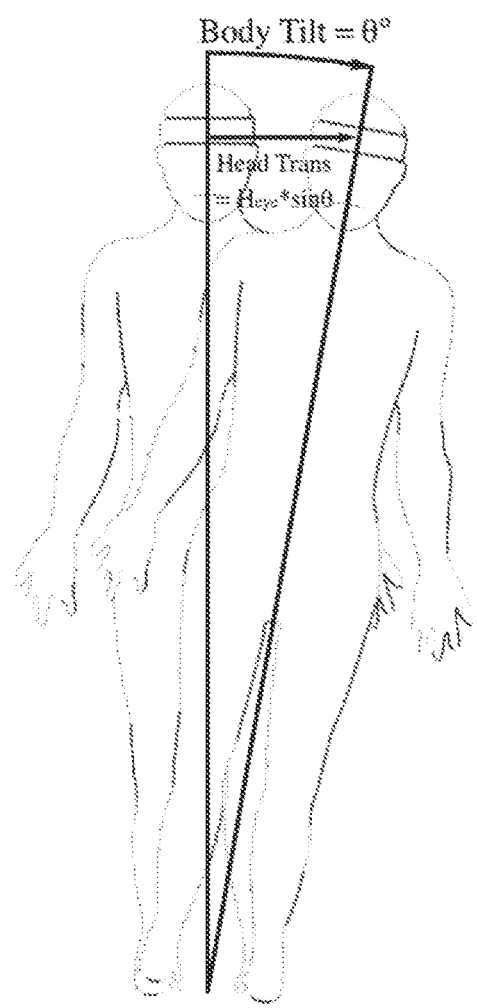
FIG. 5 is a diagram of a inverted pendulum model and a compensatory head tilt model according to one embodiment.
Figure 5:
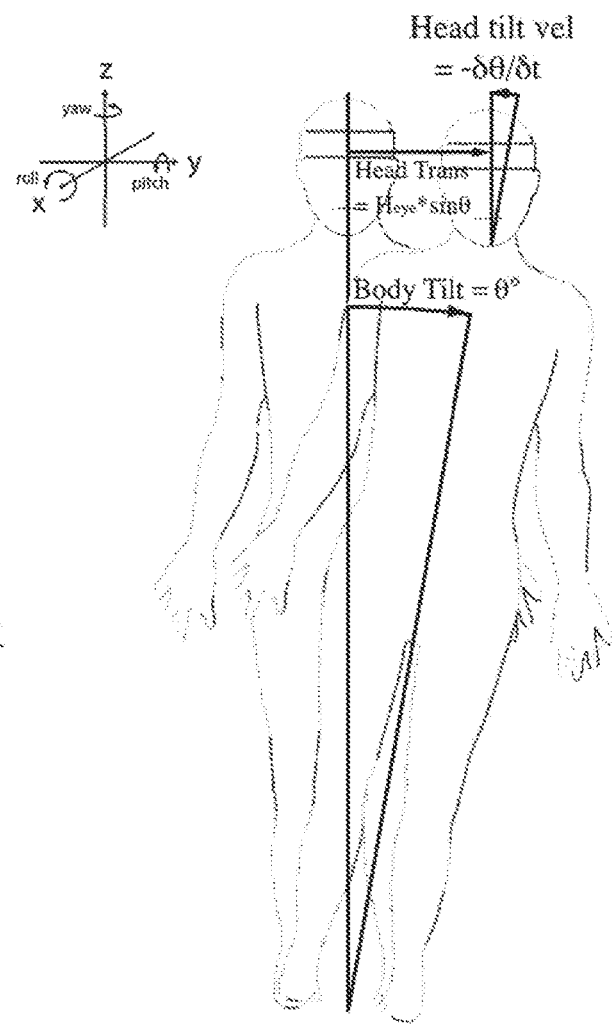

Algorithms for calculating head-centered postural stability metrics include:

Inverted Pendulum Model Algorithms (see FIG. 5, left)

Use translation in horizontal plane (x-y) at subject eye height ($H_{eyes}$) where the sensors are located in the HMD.

Anterioposterior (AP=x) head translation:

$$AP_{trans} = H_{eyes} * \sin(\theta_{pitch})$$

Mediolateral (ML=y) Head Translation:

$$ML_{trans} = H_{eyes} * \sin(\theta_{roll})$$

Head sway area=Sway ellipse defined by maximum x-y head translation:

This can be calculated by finding the $1^{st}$ and $2^{nd}$ eigenvectors from a principal component analysis.

AP head sway variability=Standard deviation of AP head translation time series.

ML head sway variability=Standard deviation of ML head translation time series.

Head Compensatory Tilt Model Algorithms (see FIG. 5, right)

Additional second and third order variables, angular velocity and angular acceleration derived from compensatory head stabilizing pitch and roll motions can supplement algorithms from Inverted Pendulum Model.

Head roll velocity=$\delta\theta_{roll}/\delta t = \dot{\theta}_{roll}$

Head pitch velocity=$\delta\theta_{pitch}/\delta t = \dot{\theta}_{pitch}$

Head roll acceleration=$\delta\dot{\theta}_{roll}/\delta t = \ddot{\theta}_{roll}$ Head roll acceleration=$\delta\dot{\theta}_{pitch}/\delta t = \ddot{\theta}_{pitch}$ The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A device for assessing the static balance impairment of a standing subject comprising:
    a head-mounted display comprising a set of at least one display panels;
    an orientation sensor;
    a stationary soft material pad configured to impede the subject from maintaining balance while standing on the pad;
    a computing device; and
    a non-transitory computer readable medium with instructions stored thereon, that when executed by a processor, perform a method comprising:
        instructing the subject to stand on the stationary soft material pad;
        presenting a sequence of scene protocols to the set of at least one display panels;
            wherein the scene protocols comprise a scene protocol that changes in at least a partially arbitrary manner;
        recording a set of measurements from the orientation sensor and a set of time indices during the sequence of scene protocols; and
        calculating a static balance score by referencing the set of measurements from the orientation sensors and the set of time indices to the sequence of scene protocols.

2. The balance assessment device of claim 1, further comprising a camera;
    wherein the computing device further records a set of camera frames from the camera; and
    wherein the computing device further refines the calculated balance score by evaluating the set of camera frames referenced to the sequence of scene protocols.

3. The balance assessment device of claim 2, wherein the camera is physically attached to the display.

4. The device of claim 3, wherein the camera is directed away from the face of the subject.

5. The device of claim 1, wherein the orientation sensor is selected from an accelerometer, a gyroscope, or a magnetometer.

6. A method of assessing the static balance impairment of a standing subject comprising the steps of:
    positioning the subject in a static standing position on a stationary soft material pad designed to impede the subject from maintaining balance while standing on the pad;
    presenting the subject with a static scene on a display;
    collecting a first set of orientation measurements;
    presenting the subject with an unstable scene on the display;
        wherein the unstable scene is a scene that changes in at least a partially arbitrary manner;
    collecting a second set of orientation measurements;
    storing the first and second sets of orientation measurements on a computing device, referenced to a set of time indices; and
    calculating a balance score for the subject by comparing the second set of orientation measurements with the first set of orientation measurements.

7. The method of claim 6, wherein the display is a head-mounted display.

8. The method of claim 6, wherein the display is an LCD display having a display size greater than 21 inches, positioned in front of the subject.

9. The method of claim 6, wherein the display is a plurality of LCD displays positioned around the subject.

10. The method of claim 6, wherein the display comprises at least one projector configured to project an image on a surface positioned in front of the subject.

11. The method of claim 10, wherein the at least one projector is configured for rear projection, and the surface is positioned between the projector and the subject.

12. The method of claim 6 wherein the static scene is a blank screen.

13. The method of claim 6 wherein the static scene is a virtual reality scene.

14. The method of claim 6 wherein the set of orientation measurements is captured at a rate of approximately 100 Hz.

15. The method of claim 6 further comprising the steps of:
    positioning the subject on an unstable surface;
    presenting the subject with an unstable scene on a display;
    collecting a third set of orientation measurements; and
    calculating a refined balance score for the subject by comparing the third set of orientation measurements to the second set of orientation measurements.

16. The method of claim 6 further comprising the steps of:
    capturing a set of images from a camera;
    performing a set of image processing operations on the set of images; and
    computing a refined balance score based on an output of the set of image processing operations.

* * * * *